United States Patent

Gryskiewicz

Patent Number: 5,618,311
Date of Patent: Apr. 8, 1997

[54] SURGICAL SUBCUTICULAR FASTENER SYSTEM

[76] Inventor: Joseph M. Gryskiewicz, 10405 Fawns Way, Eden Prairie, Minn. 55437

[21] Appl. No.: 313,761

[22] Filed: Sep. 28, 1994

[51] Int. Cl.⁶ ................................................. A61B 17/04
[52] U.S. Cl. ......................... 606/216; 606/219; 606/221
[58] Field of Search ...................... 606/215, 216, 606/142, 143, 219, 221

[56] References Cited

U.S. PATENT DOCUMENTS

| | | | |
|---|---|---|---|
| 4,899,744 | 2/1990 | Fujitsuka et al. | 606/216 |
| 5,035,692 | 7/1991 | Lyon et al. | 606/143 |
| 5,158,566 | 10/1992 | Pianetti | 606/216 |
| 5,236,440 | 8/1993 | Hlavacek | 606/216 |

*Primary Examiner*—Gary Jackson
*Attorney, Agent, or Firm*—Merchant, Gould, Smith, Edell, Welter & Schmidt

[57] ABSTRACT

A biodegradable, subcuticular surgical clip having a pair of interconnected arms each having piercing prongs directed toward the other arm is provided. The fastener does not have interlockable members.

10 Claims, 6 Drawing Sheets

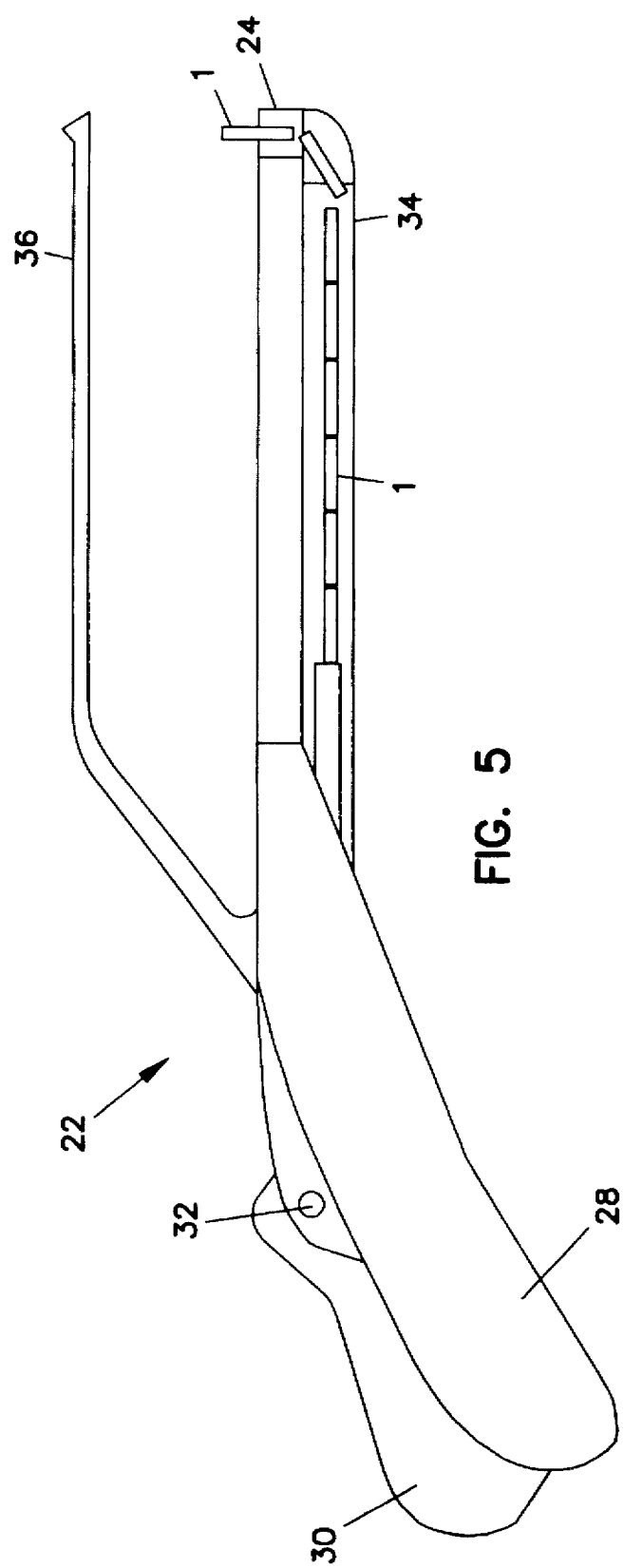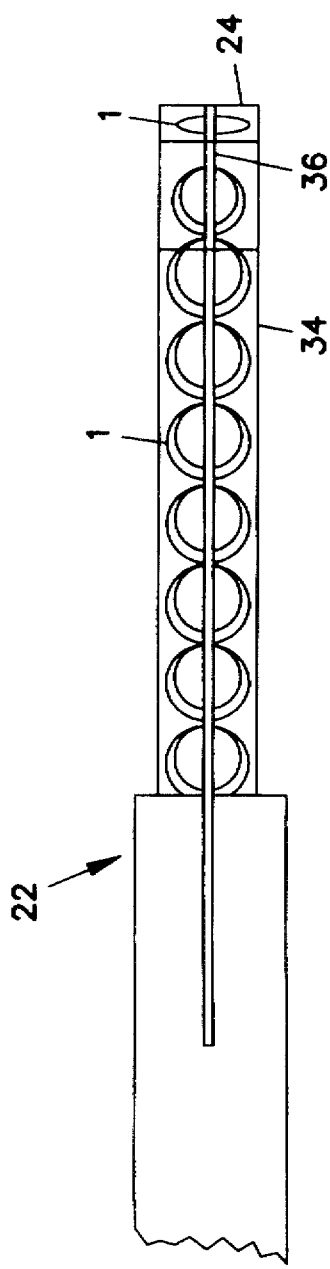
FIG. 5
FIG. 6

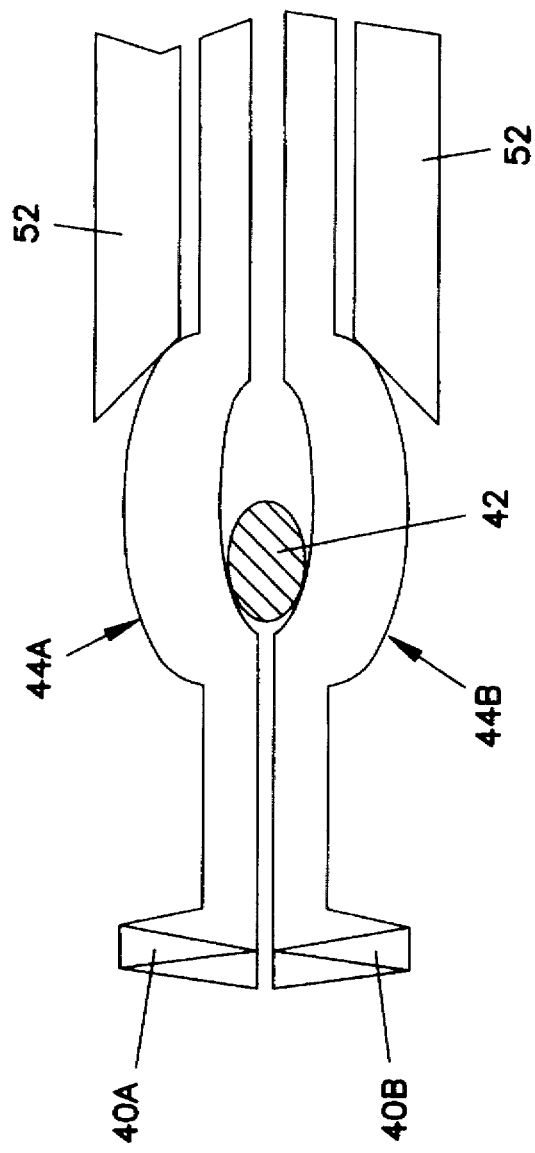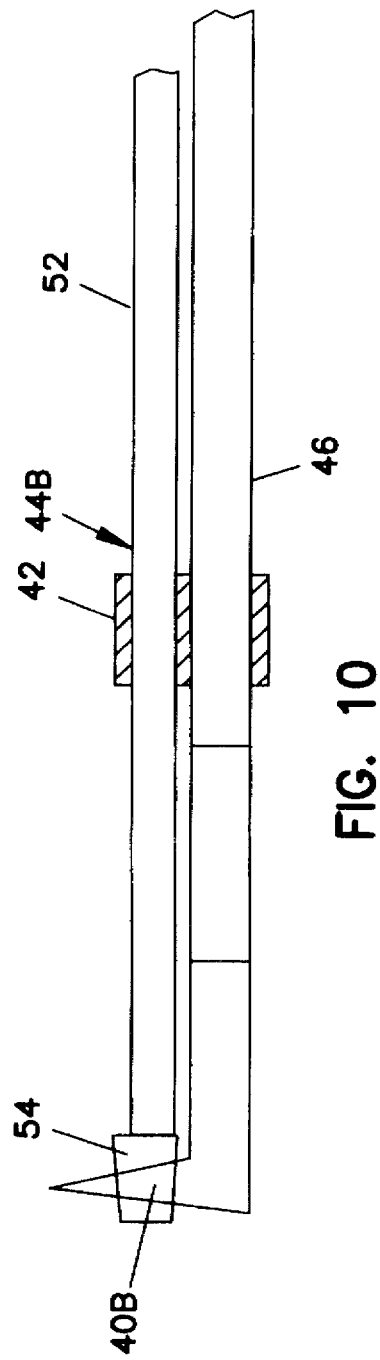

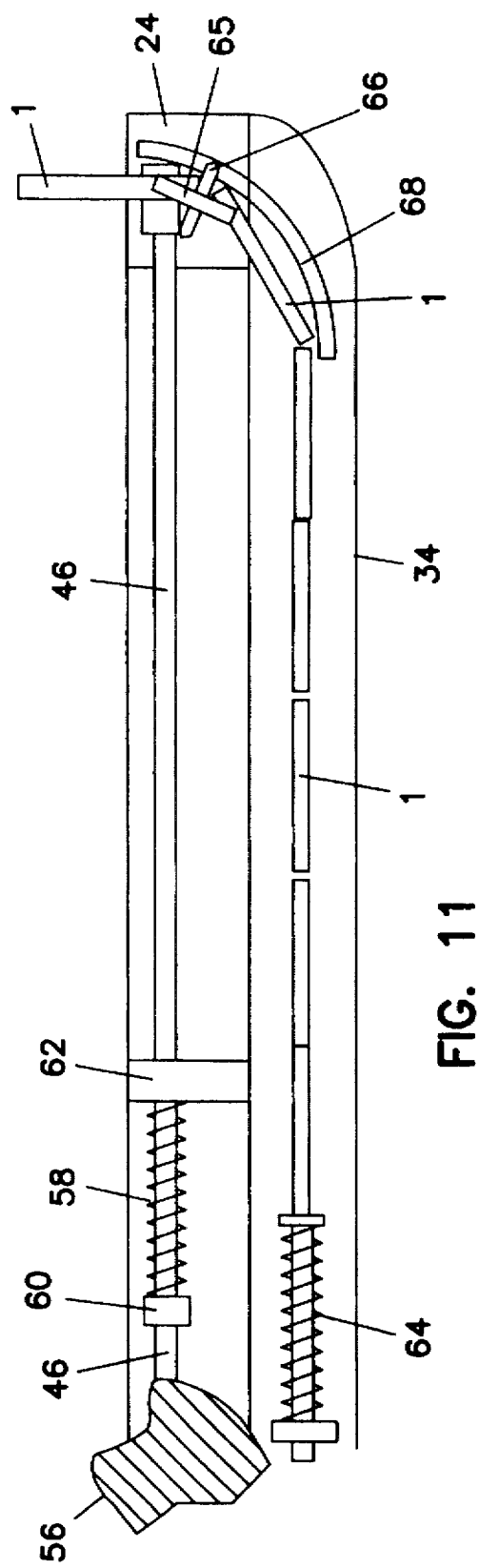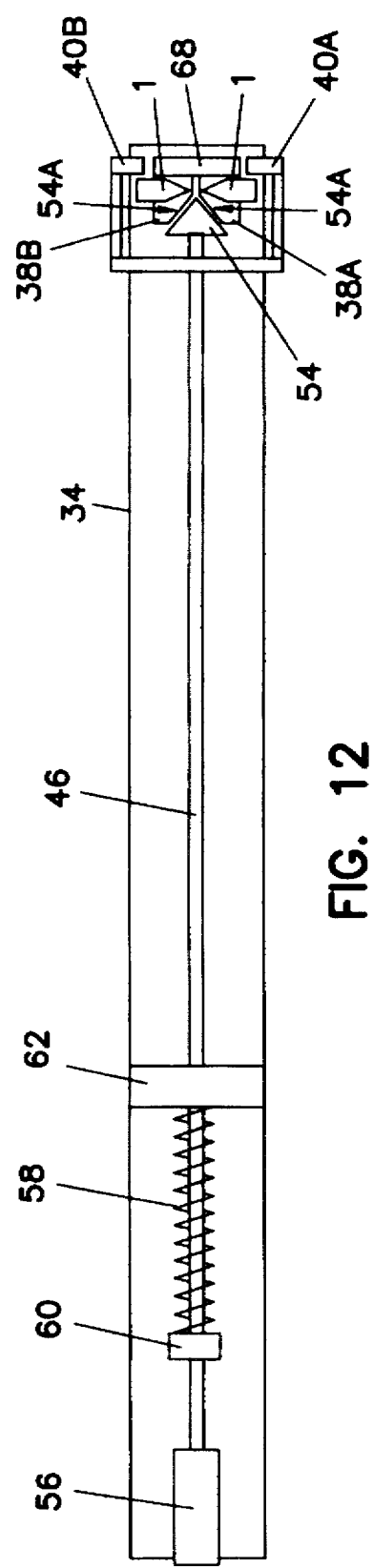
FIG. 11
FIG. 12

SURGICAL SUBCUTICULAR FASTENER SYSTEM

FIELD OF THE INVENTION

The present invention relates to surgical fasteners, and more particularly to a subcuticular clip for closing skin incisions, and an apparatus for deploying and applying such fasteners in tissue.

BACKGROUND

Surgical fasteners (including clips and staples) permit the surgeon to rapidly close a wound with a mechanical fastener which holds the tissue together while the wound heals. Both metallic and non-metallic fasteners are in common use. Some of the non-metallic fasteners are formed from bioabsorbable resinous materials such as blends of lactic acid/glycolide copolymer. Plastic materials of this type are widely known and commercially available under the trade names of "POLYSORB" and "LACTOMER" plastic. Typically fasteners made from these materials lose a substantial portion of their tensile strength after a few weeks of exposure to human tissue. After deployment in a mammalian body, the fasteners fragment and the pieces are metabolized by the body and therefore dissolve over time. In many applications the material is dyed to enhance visibility when the fastener is deployed. However, such dyed material can lead to an undesirable coloring or "tattooing" effect.

The principal advantage of surgical stapling is the speed with which a wound or incision can be closed. However, in certain surgical procedures it is desirable to close the skin wound with sutures lying completely in the dermis layer. This form of subcuticular suturing minimizes the occurrence of visible scarring. However, such subcuticular suturing is very tedious and is very time consuming to perform. At present surgical staplers and clips are not available for performing this type of closure.

An example of a surgical stapler is taught by U.S. Pat. No. 4,593,843 to Saravis. This patent teaches the use of a magazine feed stapler which delivers staples or the like at an advantageous angle.

An example of an absorbable fastener is taught by U.S. Pat. No. 4,646,741 to Smith. This patent teaches both a two piece staple and a ligating clip.

SUMMARY OF INVENTION

The present invention provides a biodegradable surgical fastener having noninterlockable members. The fastener comprises a first arm and a second arm integrally interconnected to each other. Each arm has a distal prong such that each of the distal prongs are directed toward the other arm.

The present invention also provides a surgical fastener applicator for applying surgical fasteners having arms each with a prong. The applicator comprises a fixed handle, a movable applicator lever mounted for motion with respect to said fixed handle, an applicator nose mounted to the fixed handle for storing a plurality of the fasteners and for positioning a fastener at the distal end of the applicator nose, spreader pins located proximate the applicator nose and contacting the fastener, and means connected to the spreader pins and the applicator lever for translating the movement of the applicator lever to the spreader pins. As the applicator lever is actuated, for example, when it is moved into the fixed handle, the spreader pins first apply pressure on the arms to spread apart the prongs of the fastener and subsequently release the pressure on the arms to allow the prongs to approach each other.

The applicator can further have squeezer jaws located proximate the applicator nose and coupled to the movable applicator lever so that motion is translated from the applicator lever to the squeezer jaws when the applicator lever is actuated, for example, when the lever is moved into the handle. The squeezer jaws first open to allow the prongs to be spread apart by the spreader pins and subsequently close to apply pressure on the arms to bring the prongs of said fastener together after the spreader pins release the pressure on the arms to allow the prongs to approach each other.

The present invention further provides a method for surgically fastening tissue. The method comprises a number of steps. First, a biodegradable surgical fastener having noninterlockable members is brought proximate the tissue to be fastened. This fastener comprises a first arm and a second arm integrally interconnected to each other. Each arm has a distal prong and each of the distal prongs is directed toward the other arm. Then the prongs of the first arm and the second arm are spread apart so that the tissue to be fastened is disposed between the prongs. Subsequently, the prongs are returned to the configuration that existed prior to the spreading of the prongs.

The fasteners of the present invention do not contain hinges or interlocking means such as clasp arms and can be advantageously applied to fasten severed, cut or torn tissues. Furthermore, the fasteners of the present invention can be a one-piece device which can fasten tissue without connecting or interlocking with another piece of device. It can be made without notches, grooves, barbs, and the like so that the surface of the fastener is smooth thereby facilitating the penetration of the prongs into the tissue.

Generally, biodegradable, polymeric materials are not as mechanically strong as metals. When a biodegradable polymeric fastener is deformed for a long period of time, it becomes weakened, especially in the area that has undergone significant deformation. The fastener can be deformed to an extent that, after deployment, the fastener will not be able to retain the desired configuration to hold the tissue in a closed condition. To compensate for this shortcoming, some prior art fasteners have interlocking means connected to penetrating arms to hold the fastener in a desired configuration after deployment. However, such fasteners are expensive to manufacture.

During deployment, to open the fastener before penetrating the tissue, the fastener of the present invention is flexed over a large area, rather than in a localized area of the fastener. Further, the flexion of the fastener only lasts a short period of time (fractions of a second to seconds) and therefore will not cause permanent deformation or significant weakening of the fastener.

The structure of the fastener of the present invention is relatively simple and can be easily constructed and applied. The fastener does not have interlockable members and thus no members are interlocked either in the normal, resting configuration or in the deployed configuration. The absence of interlocking members prevents the fastener from experiencing prolonged stress. Also, the absence of such interlocking members or other protrusions in the fastener enables the fastener to be deployed without using a complex, large, or cumbersome applicator. This is particularly important in subcuticular application wherein space is limited. Using a large, cumbersome instrument in a limited space can cause trauma to the tissue.

The applicator of the present invention, because of its relatively simple construction, made possible by the simple configuration of the fasteners, can be used with little intrusion under the skin. The applicator further can be used to deliver the fastener in an upward or downward direction by rotating an end effector. This allows the applicator to be conveniently used to fasten tissue from above the epidermis or subcuticularly. Furthermore, the presence of a dorsal indicator arm in the applicator obviates the need of using dyed fasteners.

BRIEF DESCRIPTION OF THE DRAWINGS

Illustrative embodiment of the invention are shown in the various figures. Throughout the figures, identical reference numerals refer to identical structural elements, wherein:

FIG. 5 is a side view of a preferred embodiment of the surgical fastener applicator of the present invention;

FIG. 6 is a top view of the front portion of the embodiment of the applicator of FIG. 5;

FIG. 9 is a plan view of a portion of an embodiment of the mechanism for spreading and closing the fastener of the embodiment of FIG. 1;

FIG. 10 is a view of a portion of an embodiment of the mechanism of FIG. 9, taken from a perspective point 90° from that of FIG. 9;

FIG. 11 is a plan side view of the embodiment of FIGS. 5 and 6, showing more details of a portion of the embodiment;

FIG. 12 is a plan top view of the embodiment of FIGS. 5 and 6, showing more details of a portion of the embodiment;

DETAILED DESCRIPTION OF PREFERRED EMBODIMENTS

Figure 1:
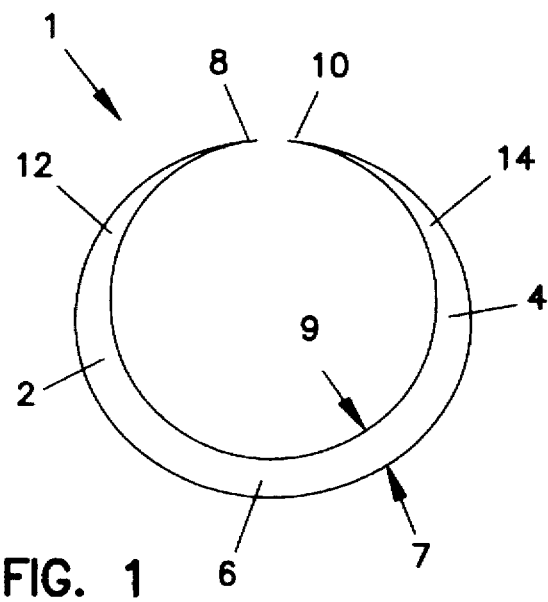
FIG. 1 is a front view of a preferred embodiment of a fastener of the present invention.
Figure 2:
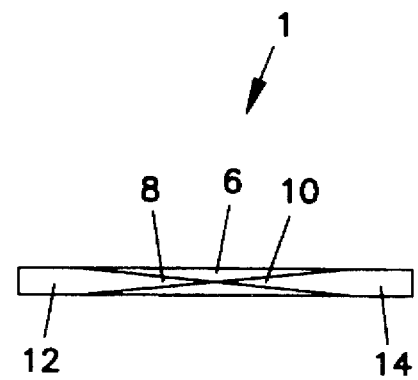
FIG. 2 is a top view of the embodiment of the fastener of FIG. 1.

The biodegradable (or bioabsorbable) surgical fastener suitable for fastening tissue comprises a first arm and a second arm integrally interconnected to each other. The first arm and second arm each have a distal prong directed toward the other arm. Referring to FIGS. 1 and 2, the preferred fastener 1 is a touch point clip (or staple). The first arm 2 and second arm 4 are integrally interconnected to form a unitary, C-shaped structure in which the tips of the prongs touch or almost touch in the normal, resting configuration (i.e., before the prongs are spread apart) as well in the deployed configuration. The first arm 2 and the second arm 4 merge together at their connecting point 6 with no hinge or similar connecting means. Preferably, the fastener has a continuously curving outwardly-facing surface 7 and a continuously curving inwardly-facing surface 9.

Preferably, the tips 8, 10 of the prongs 12, 14 are very sharp so as to facilitate penetration of tissue. Also, the middle portion of the fastener is preferably thicker than the prongs to maintain mechanical integrity when the arms 2, 4 are flexed.

Figure 3:
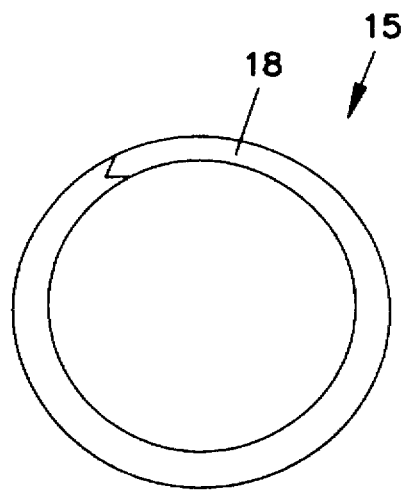
FIG. 3 is a front view of another embodiment of a fastener of the present invention.
Figure 4:
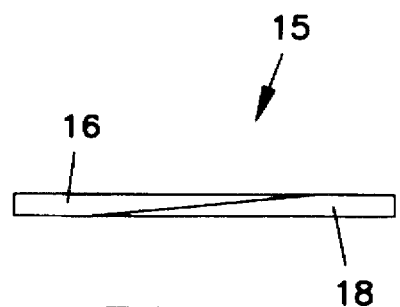
FIG. 4 is a top view of the embodiment of the fastener of FIG. 3.

Alternatively, the fastener can be a past point clip 15, as shown in FIGS. 3 and 4, which is similar to the fastener of FIG. 1 except that the tips of the prongs are past each other when the fastener is in the normal, resting configuration as well as in the deployed configuration. The prongs 16, 18 can touch each other such that viewing from the top, the clip 15 does not show any significant gap between the prongs. As used herein, the terms "top" and "up" refer to a position or direction toward the dorsal direction of the applicator for deploying the fastener when the fastener is conveniently held by a surgeon. The term "front" refers to a direction toward the nose of the applicator. Other embodiments of similar configuration will be obvious to one skilled in the art.

The fastener is made of a biodegradable material, preferably a polymeric material such as polylactide, polyglycolide, copolymer thereof, and the like. Example of polymeric material include commercially available POLYSORB and LACTOMER.

The size and shape of the fastener of the present invention are selected such that the prongs of the fastener can be spread apart to allow the tissue (i.e. the body tissue that is to be fastened together) to be disposed therebetween prior to deployment. Preferably, the fastener is constructed with the proper dimensions so that the resilient nature will return the prongs to the normal, resting configuration. Alternatively, if the tissue is too tough or hard to penetrate, the resilient nature of the fastener can cause the prongs to close to a configuration slightly more open (or spread apart) than its normal, resting configuration but still is able to retain the tissue in a closed condition. Another alternative is for the surgeon to press (or squeeze) the arms of the fastener to assist the penetration of the prongs into the tissue. After deployment, the fastener preferably has adequate mechanical integrity to maintain the normal, resting configuration until it disintegrates due to biodegradation.

PREFERRED MODE FOR CARRYING OUT THE INVENTION

The fasteners of the present invention can be deployed or applied to fasten tissue by using a surgical fastener applicator (or clip applicator). Referring to FIGS. 5 and 6, the preferred applicator 22 has a nose 24 in which a fastener, for example, a clip 1, of the present invention is positioned for deployment in the tissue. The applicator 22 can have a dorsal indicator arm 36 positioned on the centerline thereof. Preferably, at least a part of the surface of the nose 24 is transparent to permit the surgeon to view the content of the nose so that the position of the fastener 1 can be ascertained. The nose 24 of the applicator 22 can be constructed to store a number of fasteners so that after a fastener has been deployed, another one can be advanced to a position suitable for deployment.

Referring to FIG. 5, the applicator 22 has a fixed handle 28 and a movable applicator lever 30. The movable applicator lever 30 is preferably pivotally mounted to the fixed handle 28, for example, with a hinged pin 32. Preferably, the applicator lever 30 has an integral ratchet mechanism (not shown), which prevents backward motion of the applicator lever until the entire fastener application cycle for the deployment of one fastener is completed.

A rotatable applicator nose arm 34 is attached to the fixed handle 28. By rotating the rotatable applicator nose arm 34, the nose 24 can be moved to either pointing toward or away from the dorsal direction so that the fastener 1 can be delivered in an upward direction (as in fastening subcutaneous tissue) or in a downward direction (as in fastening tissue from above the epidermis).

Preferably, the applicator 22 has a removable dorsal indicator arm 36 connected to the fixed handle 28 and positioned above the level of the applicator nose 24 to indicate the position of the nose so that the surgeon can judge the position of the fastener (for example, in fastening subcutaneous tissue) before deploying the fastener.

Figure 7:
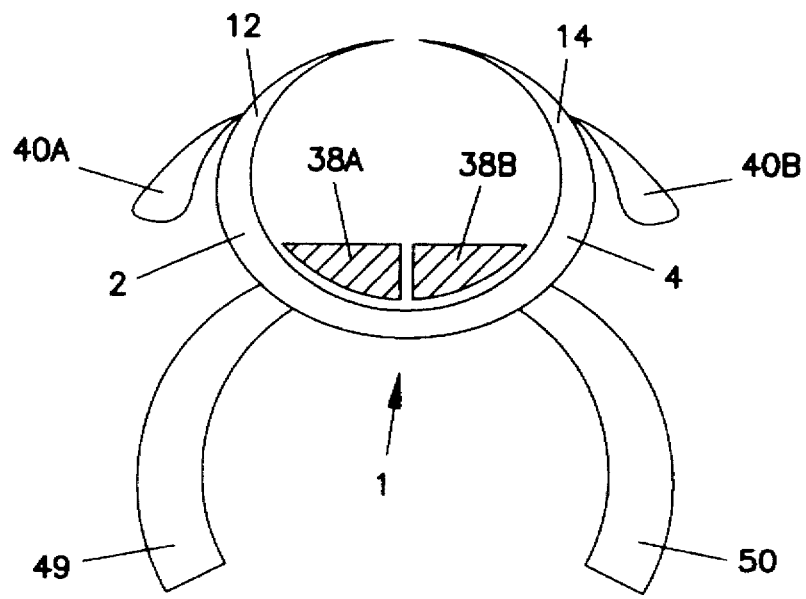
FIG. 7 is a front view showing the details of a portion of the nose of the applicator of FIGS. 5 to 6, showing spreader pins enclosed by a fastener in a resting position.
Figure 8:
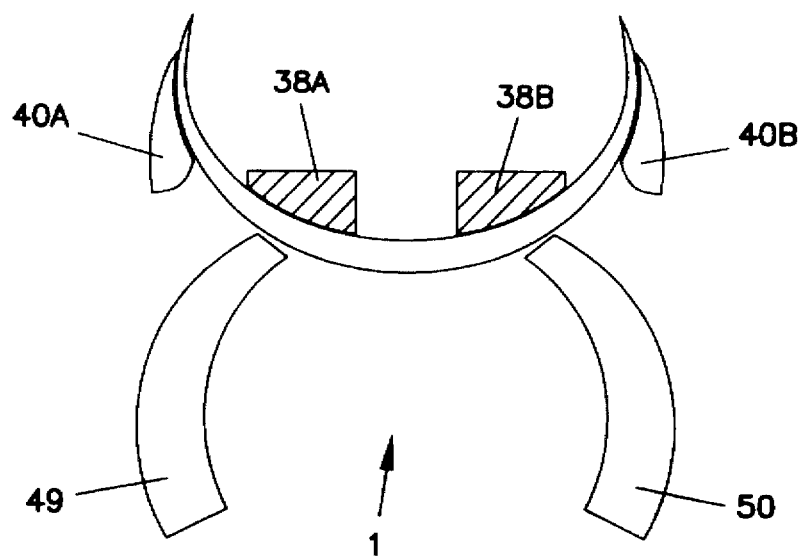
FIG. 8 is a front view of an embodiment of the mechanism of FIG. 6, showing a spread fastener.

Referring to FIGS. 7 and 8, the applicator can have spreader pins 38A, 38B in the nose for spreading apart the prongs 12, 14 of a fastener, for example, a clip 1, to enclose the tissue to be fastened before deployment of the fastener. Because of the preferred arcuate shape of the fastener, the outward movement of the spreader pins 38A, 38B along the inside arcuate surface of the fastener would force the arms 2,4 of the fastener to spread out.

Preferably, in the nose 24 of the applicator 22 are also squeezer jaws 40A, 40B for pressing the arms 2, 4 of the fastener together after the prongs have been spread apart to enclose the targeted (or desired) tissue. The squeezer jaws 40A, 40B are particularly useful in fastening tissue that is hard to penetrate such as fascia because in some cases, wherein the tissue is hard, the resilient nature of some nonmetallic, polymeric fasteners may not be adequate to cause the prongs to penetrate the tissue and return to the configuration prior to being spread (the "prespread configuration").

Various mechanisms can be used to cause the desired movement of the spreader pins and the squeezer jaws as the applicator lever is actuated (or pressed against the fixed handle). For example, as shown in FIGS. 9 and 10, the mechanism that translates the movement of the applicator lever 30 to the spreader pins (not shown in FIGS. 9 and 10) and squeezer jaws 40A, 40B can have a jaw opening pin 42 disposed between legs 44A, 44B connected to the squeezer jaws to open the squeezer jaws during the first phase of the fastener deployment by actuation of the applicator lever 30.

During this first phase of fastener deployment, the spreader pins 38A, 38B can be forced to move away (i.e., in an outward direction) from each other, for example, by an actuator arm 46 advancing between the spreader pins (as shown in FIG. 12). Because the fastener 1 is supported in the nose of the applicator 22 at where the two arms are connected together by an arcuate support, as shown in FIGS. 7 and 8, this outward movement of the spreader pins presses the arms 2, 4 and force the fastener 1 against the support and spread apart the prongs (i.e., move them away from each other). The support in the nose can be the ratchet arms 49, 50 that confine the fasteners stored in the applicator and release one fastener at a time for deployment for each cycle of the movement of the applicator lever 30. The actuator arm 46 and the jaw opening pin 42 can be mechanically linked to the applicator lever 30 for translation of movement therefrom.

The applicator can also include an assisting squeezer 52 for forcing the closure of the squeezer jaws 40A, 40B during the second phase of the fastener deployment. During this second phase of fastener deployment, the actuator arm 46 can be retracted to cause the spreader pins 38A, 38B to release the pressure on the arms of the fastener so that they can return to the prespread configuration. Simultaneously, the jaw opening pin 42 can be retracted to allow the squeezer jaws 40A, 40B to return to their closed positions and the assisting squeezer 52 can press on the legs 44A, 44B connected to the squeezer jaws to close them. The pressure by the assisting squeezer 52 can be provided, for example, by a spring (not shown). The first and second phase movement of the various components, such as spreader pins, squeezer jaws, and the like, of the applicator can be effectuated by translating the movement of the applicator lever, for example, by the operation of a properly constructed translating mechanism comprising a cam.

Referring to FIGS. 11 and 12, the actuator arm 46 can have a wedge-shaped end 54 that can be pushed between the spreader pins 38A, 38B to spread them apart. The spreader pins 38A, 38B preferably each has an inclined surface 54A, 54B with respect to the actuator arm 46 axis to receive the pushing action of the wedge-shaped end 54 of the actuator arm. As the wedge-shaped end 54 of the actuator arm 45 slides along the inclined surfaces 54A, 54B of the spreader pins, the spreader pins are forced to move away from each other, thereby spreading apart the arms 2,4 of the fastener 1.

The actuator arm 46 is preferably slidably connected to a cam 56, which can be actuated by the applicator lever 30. The actuator arm 46 can be held against the cam 56 by a spring 58. The spring 58 can be confined by a first spring limit block 60 secured to the actuator arm 46 and a second spring limit block 62 secured to the nose arm 34 of the applicator. The spreader pins 38A, 38B and the actuator arm 46 can be so configured (not shown in the drawing) that the spreader pins are movably associated with the wedge-shaped end 54 and yet both the wedge-shaped end and the spreader pins can be withdrawn, by the action of the spring moving actuator arm 46, from the front end of the nose for a sufficient distance while a new fastener is being loaded into the nose for deployment. The spring 58 maintains pressure on the actuator arm 46 to hold it against the cam 56 so that when the applicator lever 30 is returned to the rest position (i.e., fully open position with respect to the fixed handle) the actuator arm is retracted from the nose 24 of the applicator to allow a new fastener to be advanced into position.

Additional fasteners are stored in the arm, as shown in FIGS. 11. Preferably, the fasteners are under pressure from a fastener-moving mechanism which can contain a fastener-pushing spring 64. The fastener-pushing spring 64 causes the fasteners to advance to the front of the nose arm 34 as needed. Fastener ratchet 65 can be used to allow only one fastener at a time to advance into the nose and act as a support for spreading the arms of the fastener once the fastener is so advanced. The fastener ratchet 65 can be adapted to pivot on a ratchet pivot 66 so that as a fastener is released from the nose in deployment, the fastener ratchet pivots to allow the next fastener 1 to move into position in the nose 24. The ratchet can have two ratchet arms 49, 50.

As the fastener 1 is advanced to the nose 24, it can be guided into position by a guide 68. The guide 68 can also act as a stop against which the spread pins 38A, 38B can rest as the wedge-shaped end 54 of the actuator arm 46 is pushed against the spread pins to spread them. The above preferred embodiment of the applicator is for illustrative purpose and it is understood mechanism similar to the above-described can be constructed and operated by one skilled in the art.

Figure 13:
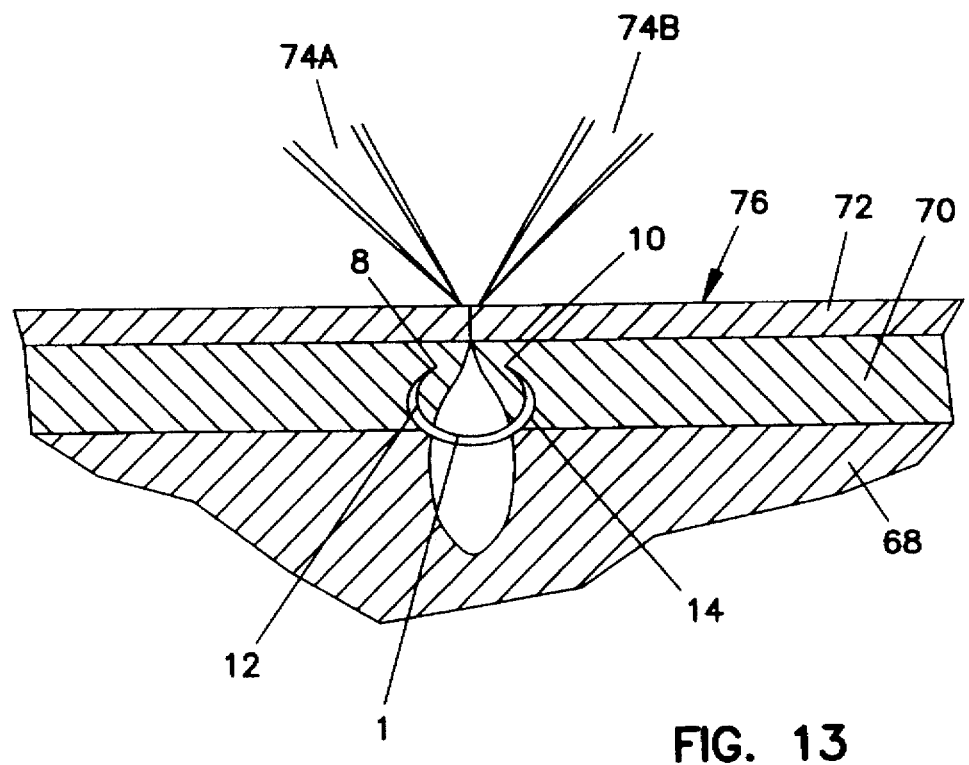
FIG. 13 is a view showing the fastener of the embodiment of FIG. 1 being deployed.
Figure 14:
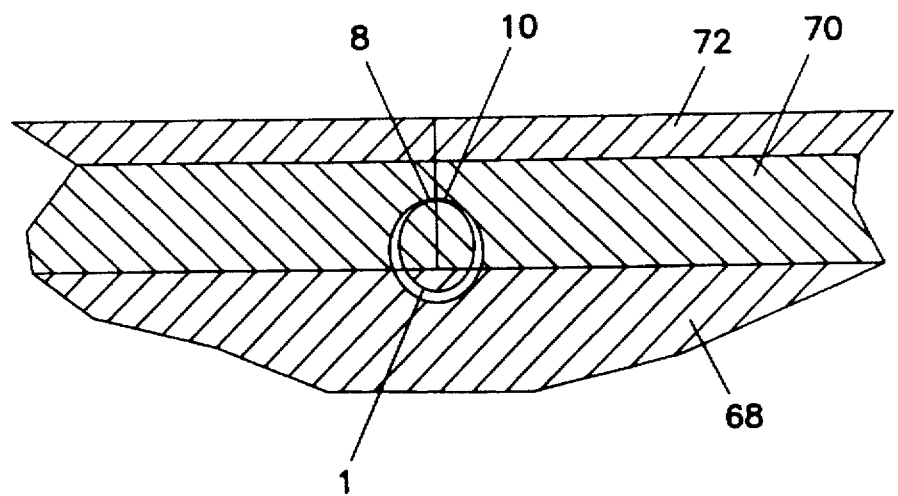
FIG. 14 is a view showing the fastener of the embodiment of FIG. 1 after deployment.

Now referring to FIGS. 13 and 14, in use, the fastener, for example, clip 1, of the present invention is brought proximate to the tissue to be fastened, for example, subcutaneous tissue 68 and dermis 70, the arms 24 (and therefore the prongs 12, 14) of the fastener are spread open by actuating the applicator lever so that the prongs enclose said tissue in the first phase of fastener deployment. When the tissue is disposed between the prongs 12, 14 in a desired position, the applicator lever 30 is further actuated to return the prongs to the prespread position (the second phase of fastener deployment), thereby penetrating and fastening the tissue. In the preferred embodiment wherein the applicator has an assisting squeezer for forcing close the prongs 12, 14, the assisting squeezer is actuated to apply pressure on the legs 44 connected to the squeezer jaws 40A, 40B in the second phase.

Generally, the tissue to be fastened is brought together before the fastener is deployed therein. For example, to fasten the subcutaneous tissue 68 and the dermis 70 but not the epidermis 72, an assistant can use forceps 74A, 74B to hold together the epidermis on top of the dermis and subcutaneous tissue as the fastener is being deployed. During deployment of the fastener, the surgeon inserts the applicator nose 24 below the tissue plane 76 to a desired location indicated by the dorsal indicator arm 36 of the applicator 22, which is located above the tissue plane 76. Actuating the applicator lever 30 will cause the fastener to emerge from the nose 24, open the prongs 12, 14 and cause the prongs to penetrate the subcutaneous tissue 68 and dermis 70, thus bringing the severed tissue together.

When properly deployed, the prongs of the fastener such as one shown in FIG. 1, will be disposed in the dermis while the balance of the fastener will be displaced in the subcutaneous tissue. After deployment of a desired number of fasteners, the applicator is then removed. The fasteners will remain in place to retain the tissue in a closed condition until they are biodegraded.

Although several illustrative embodiments of the present invention are shown and described herein, it is understood that modifications within the scope of the present invention, especially in shapes and dimension, will be apparent to one skilled in the art. For example, although a living hinge is preferred for movement of actuator lever relative to the fixed handle, a pin pivot structure may be substituted.

What is claimed is:

1. A surgical fastener comprising:
   a body of a biodegradable plastic material having uninterrupted smooth inner and outer surfaces, said body including a first arm and a second arm, each of said arms including a proximal portion and a distal prong, said arms integrally connected to each other at said proximal portions, each of said distal prongs terminating at a tip, said tips of the distal prong of the first arm and the distal prong of the second arm face each other in a noninterlocking manner;
   said plastic material being a resilient material to permit movement of said first arm and said second arm between a first relaxed position where said body is substantially closed and a second stressed position where said body is open;
   said first and second arms each having a cross-sectional area of a first thickness and tapering inward along each of said respective arms from said proximal portions toward said respective tips, said tips having a cross sectional area of a second thickness, said second thickness being less than said first thickness;
   a longitudinal axis extending through the geometric center with respect to said body, and a transverse plane bisecting said longitudinal axis substantially perpendicularly; and
   said tips aligning along said transverse plane when in both said first relaxed position and said second stressed position.

2. The fastener according to claim 1, wherein the body is one integral unit and is C-shaped, said body additionally including a midpoint where said first arm and said second arm connect, said midpoint having a rectangular shaped cross-sectional area.

3. The fastener according to claim 1, wherein the body has an arcuate shape having continuously curving outwardly-facing and continuously curving inwardly-facing surfaces.

4. The fastener of claim 1, wherein said second thickness is a point thickness.

5. The fastener of claim 1, wherein said tips of the distal prong of the first arm and the distal prong of the second arm abut each other.

6. A surgical clip applicator for applying surgical clips having arms each with a prong, the applicator comprising:
   a fixed handle;
   a movable applicator lever mounted on the fixed handle for motion with respect thereto;
   an applicator nose mounted to the fixed handle for storing a plurality of the clips and for positioning an open clip at the distal end of the applicator nose;
   spreader pins located proximate the applicator nose and coupled to the movable applicator lever, whereby motion is transferred from the applicator level to the spreader pins as the lever is moved into the handle; and whereby the spreader pins first apply pressure on the arms to spread apart the prongs of the clip and subsequently release the pressure on the arms to allow the prongs to approach each other; and
   squeezer jaws located proximate the applicator nose and coupled to the movable applicator lever, whereby motion is transferred from the applicator lever to the squeezer jaws as the lever is moved into the handle; whereby the squeezer jaws first open to allow the prongs to be spread apart by the spreader pins and subsequently close to apply pressure on the arms to bring the prongs of the clip together after the spreader pins release the pressure on the arms to allow the prongs to approach each other.

7. The applicator of claim 6 further comprising:
   a dorsal indicator means attached to the fixed handle and extending to a position proximate the distal end of the applicator nose, whereby the dorsal indicator means indicates the location of the distal end of the applicator nose.

8. The applicator of claim 6, further comprising:
   a dorsal indicator means attached to the top surface of the applicator nose and extending proximate the applicator nose, whereby the indicator means indicates the location of the distal end of the applicator nose.

9. A method for surgically fastening tissue, comprising:
   a) providing a surgical fastener comprising:
      a body of a biodegradable plastic material having uninterrupted smooth inner and outer surfaces, said body including a first arm and a second arm, each of said arms including a proximal portion and a distal prong, said arms integrally connected to each other at said proximal portions, each of said distal prongs terminating at a tip, said tips of the distal prong of the first arm and the distal prong of the second arm face each other in a noninterlocking manner;
      said plastic material being a resilient material to permit movement of said first arm and said second arm between a first relaxed position where said body is substantially closed and a second stressed position where said body is open;

said first and second arms each having a cross-sectional area of a first thickness and tapering inward along each of said respective arms from said proximal portions toward said respective tips, said tips of cross-sectional area of a second thickness, said second thickness being less than said first thickness;

a longitudinal axis extending through the geometric center with respect to said body, and a transverse plane bisecting said longitudinal axis substantially perpendicularly; and said tips aligning along said transverse plane when in both said first relaxed position and said second stressed position;

b) placing said surgical fastener proximate the surgical site;

c) applying a spreading force to move the arms of said fastener from said first relaxed position to said second stressed position and moving said fastener into contact with the tissue to be fastened, such that said tissue is disposed between the prongs while said arms are in said second stressed position; and d) releasing said force on the arms, thereby returning said first and second arms to said first relaxed state.

10. The method of claim 9, wherein the step of releasing said force on the arms is at a position such that the prongs penetrate subcutaneous tissue and dermis tissue, but not epidermis tissue.

* * * * *